(12) United States Patent
Joseph et al.

(10) Patent No.: US 9,393,342 B2
(45) Date of Patent: *Jul. 19, 2016

(54) LIQUID-ACTIVATED FORMULATION WITH SURFACTANT

(71) Applicant: The Procter & Gamble Company, Cincinnati, OH (US)

(72) Inventors: Laveeta Joseph, Cincinnati, OH (US); Thomas James Klofta, Cincinnati, OH (US); Sebastian V. Kanakkanatt, Akron, OH (US); Santosh B. Kanakkanatt, Akron, OH (US); William Winfield Cheeseman, Jr., Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 200 days.

This patent is subject to a terminal disclaimer.

(21) Appl. No.: 14/037,410

(22) Filed: Sep. 26, 2013

(65) Prior Publication Data

US 2014/0088532 A1   Mar. 27, 2014

Related U.S. Application Data

(60) Provisional application No. 61/837,405, filed on Jun. 20, 2013, provisional application No. 61/837,390, filed on Jun. 20, 2013, provisional application No. 61/837,394, filed on Jun. 20, 2013, provisional application No. 61/837,400, filed on Jun. 20, 2013, provisional application No. 61/837,408, filed on Jun. 20, 2013, provisional application No. 61/705,861, filed on Sep. 26, 2012.

(51) Int. Cl.
| | | |
|---|---|---|
| *C09D 11/02* | (2014.01) | |
| *A61L 15/56* | (2006.01) | |
| *C08K 13/02* | (2006.01) | |
| *C09D 11/50* | (2014.01) | |
| *C09D 11/30* | (2014.01) | |
| *A61F 13/42* | (2006.01) | |

(52) U.S. Cl.
CPC ............. *A61L 15/56* (2013.01); *A61F 13/42* (2013.01); *C08K 13/02* (2013.01); *C09D 11/30* (2013.01); *C09D 11/50* (2013.01); *Y10T 428/2817* (2015.01); *Y10T 428/2822* (2015.01); *Y10T 428/2826* (2015.01)

(58) Field of Classification Search
CPC ................................ C09D 11/50; C09D 11/30
See application file for complete search history.

(56) References Cited

U.S. PATENT DOCUMENTS

| | | |
|---|---|---|
| 3,675,654 A | 7/1972 | Baker et al. |
| 3,759,261 A | 9/1973 | Wang |

(Continued)

FOREIGN PATENT DOCUMENTS

| | | |
|---|---|---|
| JP | 2009-247409 | 10/2009 |
| JP | 2009-273417 | 11/2009 |

(Continued)

OTHER PUBLICATIONS

International Search Report, PCT/US2013/061877, mailed Jan. 8, 2014, 10 pages.

*Primary Examiner* — Veronica F Faison
(74) *Attorney, Agent, or Firm* — Kathleen Y. Carter

(57) ABSTRACT

A liquid-activated formulation is provided, comprising a liquid-activated colorant, a hydrochromic ionic compound, an opacifier, a binding matrix, and a surfactant.

17 Claims, 2 Drawing Sheets

(56) References Cited

U.S. PATENT DOCUMENTS

| | | |
|---|---|---|
| 3,848,594 A | 11/1974 | Buell |
| 3,860,003 A | 1/1975 | Buell |
| 3,929,135 A | 12/1975 | Thompson |
| 3,952,746 A | 4/1976 | Summers |
| 4,022,211 A | 5/1977 | Timmons et al. |
| 4,150,570 A | 4/1979 | Fuller |
| 4,192,311 A | 3/1980 | Felfoldi |
| 4,231,370 A | 11/1980 | Mroz et al. |
| 4,327,731 A | 5/1982 | Powell |
| 4,463,045 A | 7/1984 | Ahr et al. |
| 4,573,986 A | 3/1986 | Minetola et al. |
| 4,609,518 A | 9/1986 | Curro et al. |
| 4,610,678 A | 9/1986 | Weisman et al. |
| 4,629,643 A | 12/1986 | Curro et al. |
| 4,673,402 A | 6/1987 | Weisman et al. |
| 4,695,278 A | 9/1987 | Lawson |
| 4,699,622 A | 10/1987 | Toussant et al. |
| 4,699,885 A | 10/1987 | Melpolder et al. |
| 4,795,454 A | 1/1989 | Dragoo |
| 4,808,178 A | 2/1989 | Aziz et al. |
| 4,846,815 A | 7/1989 | Scripps |
| 4,888,231 A | 12/1989 | Angstadt |
| 4,909,803 A | 3/1990 | Aziz et al. |
| 4,931,051 A | 6/1990 | Castello |
| 4,938,753 A | 7/1990 | VanGompel et al. |
| 4,940,464 A | 7/1990 | Van Gompel et al. |
| 4,946,527 A | 8/1990 | Battrell |
| 4,963,140 A | 10/1990 | Robertson et al. |
| 4,990,284 A | 2/1991 | Lauterbach et al. |
| 5,026,364 A | 6/1991 | Robertson |
| 5,037,416 A | 8/1991 | Allen et al. |
| 5,092,861 A | 3/1992 | Nomura et al. |
| 5,151,092 A | 9/1992 | Buell et al. |
| 5,221,274 A | 6/1993 | Buell et al. |
| 5,246,433 A | 9/1993 | Hasse et al. |
| 5,260,345 A | 11/1993 | DesMarais et al. |
| 5,269,775 A | 12/1993 | Freeland et al. |
| 5,290,516 A | 3/1994 | Greco et al. |
| 5,342,338 A | 8/1994 | Roe |
| 5,435,010 A | 7/1995 | May |
| 5,518,801 A | 5/1996 | Chappell et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,591,152 A | 1/1997 | Buell et al. |
| 5,607,760 A | 3/1997 | Roe |
| 5,609,587 A | 3/1997 | Roe |
| 5,635,191 A | 6/1997 | Roe et al. |
| 5,643,588 A | 7/1997 | Roe et al. |
| 5,669,897 A | 9/1997 | LaVon et al. |
| 5,690,624 A | 11/1997 | Sasaki et al. |
| 5,766,212 A | 6/1998 | Jitoe et al. |
| 5,766,312 A | 6/1998 | Furhmann et al. |
| 5,858,788 A | 1/1999 | Habenstein |
| 5,865,823 A | 2/1999 | Curro |
| 5,897,545 A | 4/1999 | Kline et al. |
| 5,938,648 A | 8/1999 | LaVon et al. |
| 5,957,908 A | 9/1999 | Kline et al. |
| 5,968,025 A | 10/1999 | Roe et al. |
| 6,004,306 A | 12/1999 | Robles et al. |
| 6,114,170 A | 9/2000 | Habenstein |
| 6,120,487 A | 9/2000 | Ashton |
| 6,120,489 A | 9/2000 | Johnson et al. |
| 6,572,694 B2 | 6/2003 | Towe |
| 6,653,522 B1 | 11/2003 | Blumenthal et al. |
| 6,655,315 B1 | 12/2003 | Gattiglia |
| 6,772,708 B2 * | 8/2004 | Klofta et al. ........ 116/206 |
| 6,904,865 B2 | 6/2005 | Klofta et al. |
| 6,962,578 B1 | 11/2005 | Lavon |
| 7,159,532 B2 * | 1/2007 | Klofta et al. ........ 116/206 |
| 7,285,160 B2 | 10/2007 | Zhu et al. |
| 7,318,820 B2 | 1/2008 | Lavon et al. |
| 7,320,684 B2 | 1/2008 | Lavon et al. |
| 7,377,914 B2 | 5/2008 | Lavon |
| 7,736,351 B2 | 6/2010 | Lavon |
| 7,931,636 B2 | 4/2011 | Lavon |
| 8,017,827 B2 | 9/2011 | Hundorf et al. |
| 8,080,704 B2 | 12/2011 | Uchida et al. |
| 8,198,504 B2 | 6/2012 | Glaug |
| 8,206,533 B2 | 6/2012 | Hundorf |
| 8,247,237 B2 | 8/2012 | Moreton |
| 8,273,306 B2 | 9/2012 | Song et al. |
| 8,496,637 B2 | 7/2013 | Hundorf |
| 8,551,064 B2 | 10/2013 | Lavon |
| 8,828,271 B2 | 9/2014 | Zhang |
| 2003/0233082 A1 | 12/2003 | Kline et al. |
| 2004/0162536 A1 | 8/2004 | Becker et al. |
| 2004/0167486 A1 | 8/2004 | Busam et al. |
| 2005/0276937 A1 | 12/2005 | Kosth |
| 2005/0288646 A1 | 12/2005 | Lavon |
| 2006/0264860 A1 | 11/2006 | Lavon et al. |
| 2006/0264861 A1 | 11/2006 | Lavon et al. |
| 2006/0271005 A1 | 11/2006 | Lavon et al. |
| 2006/0271010 A1 | 11/2006 | Lavon |
| 2006/0293637 A1 | 12/2006 | Lavon et al. |
| 2006/0293638 A1 | 12/2006 | Lavon et al. |
| 2007/0032770 A1 | 2/2007 | Lavon et al. |
| 2007/0049897 A1 | 3/2007 | Lavon et al. |
| 2007/0066951 A1 | 3/2007 | Lavon et al. |
| 2007/0066952 A1 | 3/2007 | Lavon et al. |
| 2007/0066953 A1 | 3/2007 | Lavon et al. |
| 2007/0118088 A1 | 5/2007 | Lavon |
| 2007/0118089 A1 | 5/2007 | Lavon |
| 2007/0118091 A1 | 5/2007 | Lavon et al. |
| 2007/0156108 A1 | 7/2007 | Becker et al. |
| 2007/0167928 A1 | 7/2007 | Becker et al. |
| 2007/0173780 A1 | 7/2007 | Lavon |
| 2007/0173782 A1 | 7/2007 | Lavon et al. |
| 2007/0179464 A1 | 8/2007 | Becker et al. |
| 2008/0183149 A1 | 7/2008 | Lavon et al. |
| 2008/0208155 A1 | 8/2008 | Lavon et al. |
| 2008/0208156 A1 | 8/2008 | Lavon et al. |
| 2008/0234649 A1 | 9/2008 | Lavon et al. |
| 2008/0312617 A1 | 12/2008 | Hundorf |
| 2008/0312618 A1 | 12/2008 | Hundorf |
| 2008/0312619 A1 | 12/2008 | Ashton |
| 2008/0312620 A1 | 12/2008 | Ashton |
| 2008/0312628 A1 | 12/2008 | Hundorf |
| 2008/1321620 | 12/2008 | Ashton |
| 2009/0312738 A1 | 12/2009 | Lavon |
| 2009/0326494 A1 | 12/2009 | Uchida et al. |
| 2010/0004613 A1 | 1/2010 | Cohen |
| 2010/0012017 A1 | 1/2010 | Miller |
| 2010/0030173 A1 | 2/2010 | Song et al. |
| 2010/0262099 A1 | 10/2010 | Klofta |
| 2010/0262100 A1 | 10/2010 | Klofta |
| 2010/0264369 A1 | 10/2010 | Zhang |
| 2011/0015597 A1 | 1/2011 | Gil et al. |
| 2011/0015599 A1 * | 1/2011 | Song et al. ........ 604/361 |
| 2011/0041999 A1 | 2/2011 | Hundorf |
| 2011/0137274 A1 | 6/2011 | Klofta |
| 2011/0144603 A1 | 6/2011 | Song |
| 2011/0288513 A1 | 11/2011 | Hundorf |
| 2012/0143160 A1 | 6/2012 | Song |
| 2012/0144906 A1 | 6/2012 | Knyrim |
| 2012/0308787 A1 * | 12/2012 | Kozee et al. ........ 428/195.1 |
| 2012/0325408 A1 | 12/2012 | Hundorf |
| 2013/0066289 A1 * | 3/2013 | Song et al. ........ 604/361 |
| 2014/0088532 A1 | 3/2014 | Klofta et al. |
| 2014/0241954 A1 * | 8/2014 | Phillips et al. ........ 422/425 |

FOREIGN PATENT DOCUMENTS

| | | |
|---|---|---|
| JP | 2012-120667 | 6/2012 |
| WO | WO 0236177 A2 | 5/2002 |

* cited by examiner

LIQUID-ACTIVATED FORMULATION WITH SURFACTANT

FIELD OF INVENTION

Disclosed are liquid-activated formulations with a surfacant, for use as wetness/fluid indicators in absorbent articles.

BACKGROUND OF THE INVENTION

Many disposable absorbent articles comprise a wetness indicator. Wetness indicator compositions may comprise a colorant adapted to change in appearance, i.e., appear, disappear, change color, etc., upon contact with liquids such as urine, runny bowel movements, menses, etc., in the article. The color changing active used in many wetness indicator compositions are pH indicators such as bromocresol green or the like, which changes color from yellow to blue in the pH range of 3.8 to 5.4. Upon contact with a liquid, such as urine, the pH indicator will change colors to indicate the presence of the liquid, due to the higher pH of the urine.

However, current pH-based wetness indicators may be unreliable, having issues such as premature triggering and/or leaching, plus there are limits as to the variety of color options available. Therefore, there is a continuing need for simple wetness/fluid indicators that can provide a variety of color options, such as, for example, those disclosed in US. Patent Application Ser. No. 61/705,861. There is also a continuing need for ways to incorporate such wetness/fluid indicators into absorbent articles.

SUMMARY OF THE INVENTION

A single-layer liquid-activated formulation is provided, comprising a liquid-activated colorant, a hydrochromic ionic compound, an opacifier, a binding matrix, and a surfactant.

DETAILED DESCRIPTION OF THE INVENTION

Definitions

Figure 1:
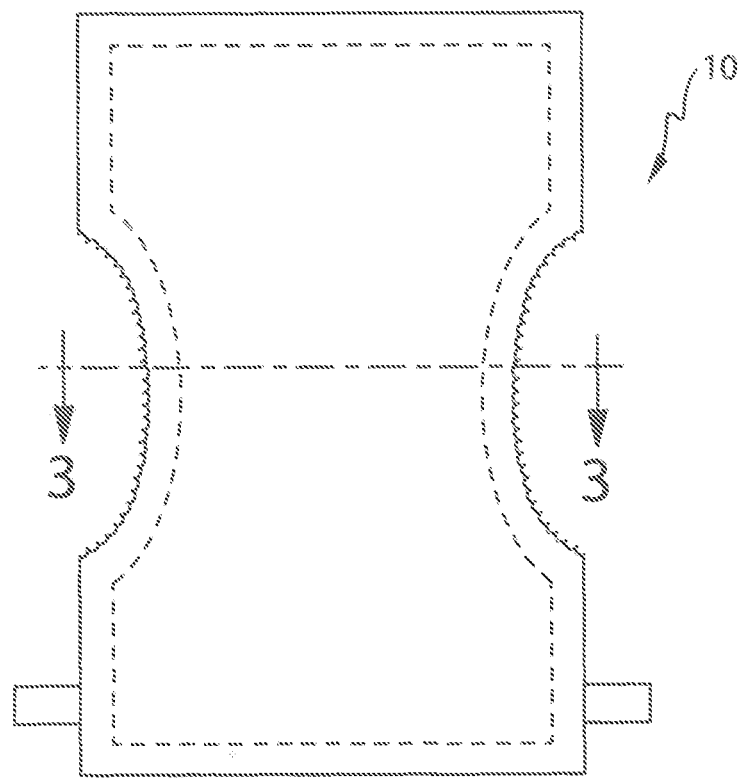
FIG. 1 is a top view of an absorbent article according to an aspect of the invention.

"Absorbent article" refers to devices which absorb and contain body exudates and, more specifically, refers to devices which are placed against or in proximity to the body of the wearer to absorb and contain the various exudates discharged from the body. Absorbent articles may include diapers, training pants, adult incontinence undergarments, feminine hygiene products, breast pads, care mats, bibs, wound dressing products, and the like. As used herein, the term "body fluids" or "body exudates" includes, but is not limited to, urine, blood, vaginal discharges, breast milk, sweat and fecal matter.

"Absorbent core" means a structure typically disposed between a topsheet and backsheet of an absorbent article for absorbing and containing liquid received by the absorbent article and may comprise one or more substrates, absorbent polymer material disposed on the one or more substrates, and a thermoplastic composition on the absorbent particulate polymer material and at least a portion of the one or more substrates for immobilizing the absorbent particulate polymer material on the one or more substrates.

"Absorbent polymer material," "absorbent gelling material," "AGM," "superabsorbent," and "superabsorbent material" are used herein interchangeably and refer to cross linked polymeric materials that can absorb at least 5 times their weight of an aqueous 0.9% saline solution as measured using the Centrifuge Retention Capacity test (Edana 441.2-01).

"Comprise," "comprising," and "comprises" are open ended terms, each specifies the presence of what follows, e.g., a component, but does not preclude the presence of other features, e.g., elements, steps, components known in the art, or disclosed herein.

"Consisting essentially of" is used herein to limit the scope of subject matter, such as that in a claim, to the specified materials or steps and those that do not materially affect the basic and novel characteristics of the subject matter.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

"Fiber" and "filament" are used interchangeably.

A "nonwoven" is a manufactured sheet, web, or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter (gsm).

"Pant" or "training pant", as used herein, refer to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants." Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999; and U.S. Ser. No. 11/197,197 to LaVon et al filed Aug. 4, 2005; Ser. No. 11/224,462 to Lavon et al filed on Sep. 12, 2005; Ser. No. 11/286,614 to LaVon on Nov. 23, 2005; Ser. No. 11/286,612 to LaVon on Nov. 23, 2005; and Ser. No. 11/709,500 issued to LaVon et al on Feb. 27, 2007.

"Substantially surfactant free" is used herein to describe an article component, such as a dusting layer, that contains less than 10% by weight of a surfactant or mixture thereof, less than 5% by weight of surfactant, less than 1% by weight of surfactant, no surfactant, or no more than an immaterial amount of surfactant where the surfactant may be anionic, cationic, nonionic, amphoteric or may include mixtures thereof and function to increase the wettability of the article component by reducing the contact angle of synthetic urine (as disclosed in U.S. Pat. No. 6,772,708 to Klofta) in contact with the surface of the article component (e.g., fibers of a nonwoven material or the surface of a film).

Binding Agents

A binding agent may be any material which immobilizes a liquid-activated colorant, or combination of colorants, within the matrix to hinder leaching of the colorant(s) into a diaper core or other regions of an absorbent article. To optimize the contrast and vibrancy of the colors, it is much preferred to "lock" the colorant within the matrix before and after contact with a fluid like urine. The binding agents can not only hinder the leaching of the color outside of the matrix, but also aid in binding the entire liquid-activated formulation to a component of the absorbent article. For example, the binder can aid in forming a strong bond between the surface of the diaper backsheet and the liquid-activated formulation. There are various materials which may be suitable for use as a binding agent in a hot melt binding matrix or solvent-based binding matrix for the liquid-activated formulations of the present invention.

In one embodiment, possible binding agents include, but are not limited to, rosins, rosin esters, polymerized rosins, pentaerythritol rosin esters, modified styrene-acrylic polymers and their salts, styrenated terpenes, polyterpene resins, terpene phenolics, and combinations thereof. Also suitable as binders are adhesives, quaternary ammonium compounds, quaternary polymers, rubbers, latexes and latex emulsions, waxes, surfactants, polyethylene glycols, polyvinyl alcohols, and combinations thereof.

A suitable rosin mixture may be the combination of Arizona Chemical's Sylvatac RE98 and Eastman's Poly-Pale™. The Sylvatac RE-98 is a pentaerythritol rosin ester and the Sylvaros PR-295 is a polymerized rosin. Both are economical matrix ingredients, both can contribute to a darker color in the dry state, both aid in maintaining effective cohesive and adhesive forces, and their acidic nature helps preserve the colorant in its dry state color. In addition to being a suitable binding agent, rosin esters, polymerized rosins, and pentaerythritol rosin esters may also be effective solubilizers for some of the other ingredients in these formulations. Furthermore, while not wishing to be limited by theory and as noted, the acidity of some rosin esters, polymerized rosins and pentaerythritol rosin esters is believed to contribute to the stabilization of particular dyes, such as, but not limited to, pH indicators. For example, some of these rosins contain acidic carboxylate groups which aid in keeping a colorant like bromocresol green (free acid) in its acidic yellow state. When using the free acid form of bromocresol green, this acidic yellow state is the preferred color for the dry state of the wetness indicator composition before the product is used.

In some embodiments, it may be preferable for the initial dry state of the wetness indicator composition to be completely white with no sign of any coloration. This can be accomplished by using synthetic ingredients that can be synthesized to be white. This is converse to the use of rosins and polymerized rosins which are natural materials most commonly derived from trees. These natural rosins tend to be more yellow in color in the dry state and not white. But, in certain cases, the addition of white opacifiers like titanium dioxide or sodium aluminum silicate can help hide the yellow coloration from the use of natural materials.

The binding material may immobilize the colorant when in its initial color state. How the binding material immobilizes the colorant when in its initial color state depends upon both what the binding material and colorant are. For example, the first binding material may work by one or more forces selected from the group consisting of adhesion, hydrogen bonding, ionic, polar covalent bonding, Van der Waals forces, dipole-dipole forces, London dispersion forces and combinations thereof.

The binding agent may be employed in compositions at levels which are effective at immobilizing and stabilizing the colorant in its first state, including from about 1% to about 90%, from about 10% to about 75%, and from about 20% to about 65%, by weight of the composition.

The binding matrix may comprise a first and second binding agent. The second binding agent may be any material which may immobilize the colorant when the colorant is in its final color state. This immobilization helps to bind the colorant within the wetness indicator composition to prevent it from leaching to other regions of the diaper such as the diaper core. It should be noted that similar to the first binding agent, the second binding agent can function not only to hinder the leaching of the colorant outside of the wetness indicator composition but the second binding agent can also aid in bonding the entire wetness indicator composition to the material of interest within the absorbent article. For example, the second binding agent may aid in bonding the wetness indicator composition to the backsheet of the diaper. There are various materials which may be suitable for use as an additional binding agent for the liquid-activated formulations of the present invention.

In one embodiment, a binding agent may be selected from, but are not limited to, the second binding agents disclosed in U.S. Pat. No. 6,904,865 to Klofta.

In one optional embodiment of the present invention, a binding agent is selected from the group consisting of quaternary ammonium salt compounds, cationic clay, polyacrylic acid polymers, organic acids, and combinations thereof. Examples of suitable quaternary ammonium compounds include, but are not limited to, dimethyl(2-ethylhexylhydrogenatedtallowalkyl) ammonium methyl sulfate, cocoalkylmethyl[ethoxylated(15)] ammonium chloride, dodecyltrimethyl ammonium chloride, hexadecyltrimethyl ammonium methyl sulfate, octadecyltrimethyl ammonium chloride, dicocoalkyldimethly ammonium chloride, di(hydrogenated tallowalkyl)dimethyl ammonium chloride, and distearyldimethyl ammonium chloride. Cationic polymers like polyethylenimines (PEI) can also function as binding agents by hindering the leaching of colorants. An example of a polyethylenimine (PEI) are the Lupasol™ line of PEI's from BASF.

It should be noted that the counter anion associated with the quaternary compound, or any binding agent having one or more cationic group, is not specifically limited to chloride. Other anions can also be employed and non-limiting examples include methyl sulfate and nitrite. Similarly, any suitable counter cation, such as, but not limited to, sodium, potassium, calcium, magnesium, zinc, protons, ammonium, substituted ammonium and the like, may be associated with a binding agent having one or more anionic groups.

The second binding material may immobilize the colorant when in its final color state. How the second binding material immobilizes the colorant when in its final color state depends upon the chemical composition of both the second binding material and colorant. For example, if the colorant's final color state is that of an anionic long chain molecule and the second binding material is a cationic molecule, then the bond formed may be, for example, an ionic bond, a covalent bond, or the like, or combinations of the relevant bonding forces. Another example, if the colorant's final color state is that of a cationic molecule, and the second binding material is an anionic long chain molecule, then the bond formed may be, for example, an ionic bond, covalent bond, or the like, or combinations of the relevant bonding forces.

In one embodiment of the present invention the second binding agent immobilizes the colorant when the colorant is in its final color state by one or more selected from the group consisting of covalent bonding, ionic bonding, Van der Waals, and combinations thereof.

Without wishing to be bound by theory, it is believed that when the colorant is an anion in its final color state and the second binding agent is a cation or the colorant is a cation in its final color state and the second binding agent is an anion, the second binding agent forms an ionically bonded coacervate with the colorant. For example, when the final state associated with a colorant's final color state is the pH of urine, contacting the colorant with urine will change the colorant to its final color state, i.e. an anion, and this forms an ionic bond with the second binding agent, which is a cation. The coacervate formation is due to the strong coulombic interaction between the opposite charges of the colorant and the second binding agent. The coacervate formed between the colorant and the second binding agent neutralizes the charge in both species and dramatically reduces both of their solubilities in polar solvents such as water or urine while the coacervate's solubility in the matrix remains high due to this charge neutralization and the coacervate's more lipophilic nature. Both of these effects dramatically inhibits the leaching of the colorant from the matrix. The increased lipophilicity of the coacervate leads to increased intermolecular bonding forces between the coacervate and components of the matrix. These intermolecular forces may further limit the diffusion and mobility of the colorant into an fluid environment such as water or urine.

In certain optional embodiments of the present invention, use of cationic quaternary ammonium compounds, quaternary polymers, and combinations thereof as the second binding agent may also function to darken or intensify the color change of certain colorants, especially those belonging to the sulfonephthalein class of pH indicators. Without wishing to be bound by theory, it is believed this darkening is due to several possible factors: 1) alkaline impurities within the quaternary ammonium raw material, 2) absorption shifting and absorptivity coefficient increases due to coacervate formation and/or 3) increased formation of the colorant in its final color state.

The second binding agent may be employed in compositions at levels which are effective at immobilizing the colorant in its second state, including from about 0.5% to about 20%, from about 0.5% to about 10%, and from about 0.1% to about 5%, by weight of the composition.

In some embodiments, the binding matrix is a solvent-based binding matrix, where possible binding agents include, but are not limited to, acrylic-based solvents, alcohol-based solvents, aqueous solvents like water, organic solvents, and combinations thereof. Examples may include vinyl based resins, acrylic resins, acrylates/ethylhexyl acrylate copolymers; sodium acrylate/sodium acryloyldimethyl taurate copolymer; ethylene-vinyl chloride emulsions, vinyl-acrylic resins, natural and synthetic alkyd resins, acrylic resins, polyester resins, natural and synthetic latex emulsions, polyurethanes, melamine resins, epoxy resins, amine resins, waxes, acrylates/octyl acrylate copolymer; ammonium polyacrylate. Examples of organic solvents may include, for example, alcohols, ketones, mineral spirits, petroleum distillates, glycol ethers, silicone fluids, oils like linseed oil, esters, ethers, amides, and or lactones with alcohol being preferred. Organic solvents may be selected from ethanol, propanol, butanol, acetone, tetrahydrofuran, benzene, toluene and acetonitrile. Polar solvents are preferred. Methanol is preferred. Other suitable binding agents may include acrylate/acrylamide copolymers and copolymers of vinylpyrrolidone and dimethylaminopropyl methacrylamide etc. The binder could be modified or incorporated with a commercialized varnish material or other encapsulating materials.

Water-soluble resins may also be suitable, as they may act as a binder and cause the colorant to adhere to the substrate. Examples include polyamide, cellulose derivatives, an acrylic polymer or a polyol, e.g. a water soluble resin selected from the group consisting of polyvinylpyrrolidone, polyvinyl alcohol, carboxymethylcellulose, poly(2-ethyl-2-oxazoline), polymers (homopolymers and copolymers) based on acrylic acid, polymers (homopolymers and copolymers) based on methacrylic acid), and polymers (homopolymers and copolymers) based on acrylamide and any combination thereof. Some organic soluble resin binders would include those based on acrylic, alkyd, amide, epoxy, nitrocellulose, phenolic, polyester, polyurethane, and vinyl monomers, oligomers and polymers.

Other suitable ink base material as binding agents for the color-changing compositions of the invention may be a varnish base such as a nitrocellulose compound based varnish, ethyl cellulose-based varnish, polyurethane based binding systems or a phenolic-modified co-solvent type polyamide resin-based varnish. It is believed that the ink base material may help the stability of the color-changing composition. It is also believed that the ink base material may improve the adhesion of the color-changing composition to the substrate.

In general, the solvent-based binding matrix may be from about 5% to about 75% by weight of the liquid-activated formulation.

Hot Melt Adhesives

In some embodiments, the binding agent may be a hot melt adhesive, in some embodiments, a solvent-based binding matrix. Additional components of a hot melt adhesive binding matrix may include base polymers, tackifiers, waxes, rubbers, solvents, wetting agents, and/or anti-oxidants. Examples of base polymers used in hot melt adhesives may include ethylene-vinyl acetate (EVA) copolymers; ethylene-acrylate copolymers; ethylene-vinylacetate-maleic anhydride terpolymer; ethylene-acrylate-maleic anhydride terpolymer; polyolefins such as low density and high density polyethylene, atacttic polypropylene, oxidized polyethylene, polybutene-1; amorphous polyolefins like amorphous atactic propylene (APP), amorphous propylene/ethylene (APE), amorphous propylene/butane (APB), amorphous propylene/hexane (APH), and amorphous propylene/ethylene/butane; polyamides; styrene block copolymers (SBC); styrene/acrylic polymers and modified styrene/acrylic polymers; polycarbonates; silicone rubbers; polypyrrole based polymers; thermoplastic elastomers like natural and synthetic polyisoprene, polybutadiene rubber, butyl rubber, chloroprene rubber, ethylene-propylene rubber, epichlorohydrin rubber, polyacrylic rubber, polyether block amides; polymers of acrylates, alkyd resins, amides, amino resins, ethylene co-terpolymer resins such as EVA, epoxy resins, fluoropolymers, hydrocarbon resins, phenols, polyesters, olefins, polyurethanes, silicones and functionalized silicones, polystyrene and polyvinyls.

Tackifiers suitable for hot melt adhesives include, without being limited to, natural resins like copals like gum copal, dammars, mastic, and sandarac; rosins and their derivatives; terpenes and modified terpenes; aliphatic, cycloaliphatic, and aromatic resins like C5 aliphatic resins, C9 aromatic resins, and C5/C9 aromatic/aliphatic resins, hydrogenated hydrocarbon resins and their mixtures.

Waxes suitable for hot melt adhesives include, without being limited to, mineral waxes like paraffin and microcrystalline waxes; polyethylene waxes; polyethylene glycol type waxes; oxidized polyethylene waxes; highly branched polymer waxes like Vybar™ from Baker Hughes; fatty amide waxes; natural and synthetic waxes like beeswax, soywax, carnuba, ozokerite, ceresin; waxes derived from both the Fisher-Tropsch and Ziegler-Natta processes; and silicone waxes.

Additional additives for adhesives and hot melt adhesives may include plasticizers, like glyceryl tribenzoate, phthalates, paraffin oils, and polyisobutylene; UV stabilizers; biocides and antimicrobial preservatives; antioxidants, like BHT, phospites and phosphates; antistatic agents; rosins and their derivatives; pigment, particle and powder wetting agents like polyhydroxystearic acid, polyglyceryl-4 isostearate, hexyl laurate, isopropyl myristate, propylene carbonate, isononyl isononanoate, glyceryl behenate/eicosadioate, trihydroxystearin, C12-15 alkyl benzoate, triethoxycaprylysilane, castor oil; and viscosity modifiers. Optionally, solvents like mineral oil, isoparaffins, alkanes like hexane, silicone fluids, esters, alcohols, polyethylene glycols, glycerin, glycols, and water can be added to reduce the viscosity of the composition or to increase the solubility of other ingredients or change other strategic properties of the wetness indicator composition.

Colorants

The liquid activated formulations which are utilized in this invention comprise a liquid-activated colorant. A colorant may be a dye, an ink, a pigment, or a pH indicator. The liquid activated colorant can be soluble within the wetness indicator composition and in certain cases, it can be suitable to homogeneously suspend or disperse the colorant within the wetness indicator composition. As noted, the colorant changes color upon coming in contact with water or urine. In some embodiments, the liquid-activated formulation may further comprise a permanent colorant that does not change color upon coming in contact with water or urine.

Some representative examples of liquid-activated colorants that can be used in the practice of this invention include: Malachite green, brilliant green, crystal violet, erythrosine B, methyl green, methyl violet 2D, picric acid, naphthol yellow S, quinaldine red, eosine Y, metanil yellow, m-cresol purple, m-cresol red, thymol blue, xylenol blue, basis fuchsin, eosin B, 4-p-aminophenol(azo)benzenesulphonic acid-sodium salt, cresol red, martius yellow, phloxine B, methyl yellow, bromophenol blue, congo red, methyl orange, bromochlorophenol blue (water soluble or free acid form), ethyl orange, fluorocene WS, bromocresol green, chrysoidine, methyl red sodium salt, alizarine red S—H2O, cochineal, chlorophenol red, bromocresol purple, 4-naphtha, alizarin, nitrazine yellow, bromothymol blue, brilliant yellow, neutral red, rosalic acid, phenol red, 3-nitro phenol, orange II, phenolphthalein, o-cresolphthalein, nile blue A, thymolphthalein, aniline blue WS, alizarine yellow GG, mordant orange, tropaolin O, orange G, acid fuchsin, thiazol yellow G, indigo carmine, cresol red, methyl red, p-nitrophenol, and alizarin yellow R. In certain instances, it is advantageous to use the free acid form, free base form, or salt form of the colorants.

Additional water-soluble colorants may include FD&C Blue No. 1, FD&C Blue No. 2, FD&C Green No. 3, FD&C Red No. 40, FD&C Red No. 4, FD&C Yellow No. 5, FD&C Yellow No. 6, C.I. Food Blue 5, and C.I. Food Red 7, D&C Yellow No. 10, D&C Yellow No. 7, D&C Yellow No. 2, D&C Yellow No. 8, D&C Orange No. 4, D&C Red No. 22, D&C Red No. 28, D&C Red No. 33, D&C Green No. 8, D&C Green No. 5, D&C Brown No. 1, and any combination thereof. Preferably, the colorant is soluble within the wetness indicator composition, but, as noted in certain instances, the colorant can function as intended by homogenerously suspending or dispersing it within the wetness indicator composition.

Many of these aforementioned colorants do not change colors when contacted by an aqueous solution like urine. These are referred to as permanent colorants which can function to change the color hue of the wetness indicator composition of either its dry state or color changed state after contact with a fluid like urine. Some examples of oil soluble permanent colorants include D&C Yellow No. 11, D&C Red No. 17, D&C Red No. 21. D&C Red No. 27, D&C Violet No. 2, D&C Green No. 6, and D&C Orange No. 5. These permanent and oil soluble colorants can not only change the color hue of the wetness indicator composition in either the dry or wet state, but they can be advantageous due to their reduced solubility in hydrophilic liquids like urine. Thus, their leaching is inhibited and they possess a higher probability of remaining bound within the wetness indicator composition after being wetting with an aqueous liquid like urine.

Additional suitable fluid colorants include water soluble colorants like direct dyes, acid dyes, base dyes, and various solvent-soluble colorants. Dispersed or suspended pigment colorants can also be employed into these wetness indicator compositions (liquid-activated formulations). Examples include, but are not limited to, C.I. Acid Yellow 73, C.I. Solvent Yellow 94, C.I. Acid Yellow 74, C.I. Solvent Orange 32, C.I. Solvent Red 42, C.I. Acid Orange 11, C.I. Solvent Red 72, C.I. Pigment Orange 39, C.I. Solvent Orange 18, C.I. Acid Red 87, C.I. Solvent Red 43, C.I. Pigment Red 90:1, C.I. Solvent Red 44, C.I. Solvent Red 45, C.I. Solvent Orange 16, C.I. Acid Red 91, C.I. Acid Red 98, C.I. Acid Red 92, C.I. Solvent Red 48, C.I. Pigment Red 174, C.I. Acid Red 95, C.I. Solvent Red 73, C.I. Pigment Red 191, C.I. Acid Red 51, C.I. Food Red 14, C.I. Pigment Red 172, C.I. Solvent Red 140, C.I. Acid Red 93, C.I. Solvent Red 47, C.I. Acid Red 94, C.I. Solvent Red 141, C.I. Mordant Violet 25, C.I. Solvent Orange 17, C.I. Solvent Red 46, D&C Red 27 (C.I. 45410:1), D&C Orange 5 (C.I. 45370:2), and combinations thereof. More preferred fluid colorants are selected from the group consisting of D&C Red 27, D&C Orange 5, and combinations thereof.

Additional suitable colorants may include bromopyrogallol red, bromoxylenol blue, methylene blue, monoazo dyes such as acid alizarin violet N, monoazo pyrazoline dyes (such as acid yellow 34), diazo dyes (such as acid black 24), anthraquinone dyes (such as acid black 48), amphoteric anthraquinone dyes (such as acid blue 45), triphenylmethane dyes (such as acid fuchsin), phthalein type dyes (such as o-cresolphthalein), xanthene dyes (such as 2'7' dichlorofluorescein eosin B), heterocyclic acridine aromatics (such as acridine orange), diphenylmethane dyes (such as auramine O), triphenylmethane dyes (such as basic fuchsin), cationic thiazine dyes (azure C), cationic anthraquinone dyes such as basic blue 47, phthalocyanine type dyes (such as strazon orange G), anthraquinone type (sch as alizarin), neutral complex dyes (such as azure A eosinate), terpene type dyes (such as trans-beta-carotene), as well as combinations including at least one of the foregoing dyes.

Examples of colorants further include, but are not limited to, organic dyes, inorganic pigments, colored macromolecules, colored nanoparticles and materials. Examples of dyes include acridine dyes, anthraquinone dyes, arylmethane dyes, azo dyes, nitro dyes, nitroso dyes, phthalocyanine dyes, quinone-imine dyes, Aazin dyes, Indophenol dyes, oxazin dyes, Oxazone dyes, Thiazole dyes, xanthene dyes, Fluorene dyes, fluorone dyes, rhodamine dyes. Examples of pigments include Cadmium pigments: cadmium yellow, cadmium red, cadmium green, cadmium orange; Carbon pigments: carbon black (including vine blac, lamp black), ivory black (bone char); Chromium pigments: chrome yellow and chrome green; Cobalt pigments: cobalt violet, cobalt blue, cerulean blue, aureolin (cobalt yellow); Copper pigments: Azurite, Han purple, Han blue, Egyptian blue, Malachite, Paris green, Phthalocyanine Blue BN, Phthalocyanine Green G, verdigris, viridian; Iron oxide pigments: sanguine, caput mortuum, oxide red, red ochre, Venetian red, Prussian blue; Clay earth pigments (iron oxides): yellow ochre, raw sienna, burnt sienna, raw umber, burnt umber; Lead pigments: lead white, cremnitz white, Naples yellow, red lead; Mercury pigments: vermilion; Titanium pigments: titanium yellow, titanium beige, titanium white, titanium black; Ultramarine pigments: ultramarine, ultramarine green shade; Zinc pigments: zinc white, zinc ferrite. Other examples include alizarin, alizarin crimson, gamboge, cochineal red, rose madder, indigo, Indian yellow, Tyrian purple, organic quinacridone, magenta, phthalo green, phthalo blue, pigment red.

Hydrochromic Ionic Compound

The hydrochromic ionic compound is typically a reactive ionic compound, such as an ionizing salt. Some representative examples of hydrochromic ionic compounds that can be employed in the practice of this invention include: lithium hydrogen sulfate, lithium hydrogen carbonate, potassium hydrogen sulfate, potassium hydrogen carbonate, rubidium hydrogen sulfate, rubidium hydrogen carbonate, cesium hydrogen sulfate, cesium hydrogen carbonate, sodium hydrogen sulfate, sodium hydrogen carbonate, sodium carbonate, cesium hydroxide, lithium hydroxide, potassium hydroxide, calcium hydroxide, magnesium hydroxide, sodium thiosulfate penta hydrate, sodium hydroxide, rubidium hydroxide, cobalt chloride, cobalt nitrate, copper sulpate copper nitrate, iron (II) sulfate, iron (III) sulfate, iron (II) chloride, iron (III) chloride, citric acid, monosodium dihydrogen citrate, disodium hydrogen citrate, trisodium citrate, gluconic acid, sodium gluconate, glycolic acid, sodium glycolate, malic acid, sodium malate, maleic acid, sodium maleate, acetic acid, phosphoric acid, trisodium phosphate, sodium dihydrogen phosphate, disodium hydrogen phosphate, monostearyl phosphate, monocetyl phosphate, monostearyl citrate, hydrochloric acid, nitric acid, sulfuric acid and combinations thereof.

Opacifiers

The opacifiers that can be utilized in the liquid activated formulations of this invention can be porosigens or antiporosigens and are typically white powders when they are in the form of dry solids (before being incorporated into the ink formulation). In the cases where the opacifiers act as porosigens they allow for liquid transmission through coatings which are applied to a substrate, such as a coating which is printed on the outer layer of a diaper. In other words, the porosigen is a compound which allows for liquid to be transmitted through it which facilitates liquid transmission throughout the coating. In the case of antiporosigens liquid transmission is attained by virtue of liquid permeable interstices which are formed in proximity to the antiporosigens by virtue of disrupting the structure of liquid barrier materials. In other words, the antiporosigens cause holes to be present in the dry coating structure which are of a size and structure which allows for liquid to flow through the coating. Some representative examples of opacifiers that can be utilized include titanium dioxide, calcium carbonate, calcium hydroxide, sodium silicate, potassium silicate, silica, starch, ethocell, methocell, barium carbonate, barium silicate, calcium silicate, aluminum silicate, aluminum hydroxide, zinc oxide, sodium aluminum silicate like Evonik's Sipernat™ 820a, zirconium silicate, magnesium aluminum silicate, and aluminum oxide. Suitable polymeric opacifiers include the styrene/acrylate copolymers like Opulyn™ 301 from Rohm and Haas, or the SunSphere™ line of opacifiers, also from Rohm and Haas.

Surfactants

The present invention includes surfactants. Surfactants that are suitable for the present invention may include, for example, tergitol, ethoxylated alcohols, fatty alcohols, high molecular weight alcohols, esters, polymers and other natural and synthetic waxes or olefininc materials as known in the art; anionic and cationic surfactants, alkoxylated alkylates such as PEG-20 stearate, end group-capped alkoxylated alcohols, alkoxylated glyceryl and polyglyceryl alkylates such as PEG-30 glyceryl stearate, glyceryl alkylates such as glyceryl stearate, alokylated hydrogenated castor oil, alkoxylated lanolin and hydrogenated lanolin, alkoxylated sorbitan alkylates, sugar derived surfactants such as the alkyl glycosides and sugar esters, poloxamers, polysorbates, and sulfo succininc acid alkyl esters. Further examples include nonionic surfactants and amphoteric surfactants and any combination thereof; specific-diethylhexylsodiumsulfosuccinate, available as MONOWET MOE75 from Uniqema. Another example is 4-1-aminoethylphenolpolyoxyethylenefattyethers, polyoxyethylene sorbitan esters, and polyoxyethylene fatty acid esters. Surfactants may comprise from about 3% to about 8% by weight of the liquid-activated formulation.

Surfactants that are suitable for the present invention may include, for example, ethoxylated alcohols, fatty alcohols, high molecular weight alcohols, ethoxylated sorbitan esters like Tween™ 40 from Croda, the ethoxylated pareth surfactants like Performathox™ 450 from New Phase Inc., esters, polymers and other natural and synthetic waxes or olefininc materials as known in the art; anionic and cationic surfactants, alkoxylated alkylates such as PEG-20 stearate, end group-capped alkoxylated alcohols, alkoxylated glyceryl and polyglyceryl alkylates such as PEG-30 glyceryl stearate, glyceryl alkylates such as glyceryl stearate, alkoxylated hydrogenated castor oil, alkoxylated lanolin and hydrogenated lanolin, alkoxylated sorbitan alkylates, sugar derived surfactants such as the alkyl glycosides and sugar esters, poloxamers, polysorbates, and sulfo succininc acid alkyl esters. Further examples include nonionic surfactants and amphoteric surfactants and any combination thereof; specific-diethylhexylsodiumsulfosuccinate, available as MONOWET MOE75 from Uniqema, the sodium dioctyl sulfosuccinate line of surfactants like Aerosol™ OT-100 from Cytec Inc. Another example is 4-1- aminoethylphenolpolyoxyethylenefattyethers, polyoxyethylene sorbitan esters, TWEEN, and polyoxyethylene fatty acid esters.

Other suitable surfactants may be neutral block copolymer surfactants, which can be selected from polyoxypropylene-polyoxyethylene block copolymer, poly [poly(ethylene oxide)-block-poly(propylene oxide)]copolymer or propylene glycol-ethylene glycol block copolymer. Suitable non-ionic surfactants include the ethxoylated sorbitan ester TWEEN™ surfactants from Croda Inc., such as TWEEN 20 surfactant, TWEEN 40 surfactant and TWEEN 80 surfactant, and TRITON X-100 surfactant, which are available from Sigma-Aldrich, Incorporated. Other suitable neutral surfactants include the sorbitan ester SPAN™ surfactants from Croda. Other non-ionic surfactant and emulsifiers include fatty alcohol ethoxylates, fatty acid alkoxylates, polol alkoxylates, and the ethoxylated, phosphate esters and ethoxylated phosphate esters, linear primary alcohols like the Performathox™ ethoxylates from New Phase Inc., polyethylene lauryl ether, polyoxyethylene nonyl phenyl ether, polyoxyethylene oleyl phenyl ether, polyoxyethylene sorbitan monolaurate, polyethylene glycol monostearate, polyethylene glycol sorbitan monolaurate, polyoxyethylenesorbitan monopalmitate, polyoxyethylenesorbitan monostearate, polyoxyethylenesorbitan monooleate, polyoxyethylenesorbitan trioleate, polypropylene glycol sorbitan monolaurate, polyoxypropylenesorbitan monopalmitate, polyoxypropylenesorbitan monostearate, polyoxypropylenesorbitan monooleate, polyoxypropylenesorbitan trioleate, polyalkyne glycol sorbitan monolaurate, polyalkyne glycol sorbitan monopalmitate, polyalkyne glycol sorbitan monostearate, polyalkyne glycol sorbitan monooleate, polyalkyne glycol sorbitan trioleate and mixtures of such neutral surfactants.

The neutral block copolymer based surfactants include FLURONIC series block copolymers, such as PLURONIC P84 or FLURONIC P85 surfactants, which are available from BASF Corporation. Super wetting surfactants like Dupont's Capstone™ line of fluorosurfactants and Siltech's Silsurfrm A008 silicone super wetter would also be suitable at lower concentrations.

Other suitable neutral block copolymer based surfactants include nonylphenol ethoxylates, linear alkyl alcohol ethoxylate, ethylene oxide-propylene oxide block copolymer, polyoxypropylene-polyoxyethylene block copolymer, polyalkylene oxide block copolymer, polyalkylene oxide block copolymer and propylene glycol-ethylene glycol block copolymer.

A surfactant or combination of surfactants may be from about 1% to about 30% by weight of the liquid-activated formulation.

Additional Ingredients

Additional ingredients may include, for example, a stabilizer, a structural adjunct, and/or solvents. When present, such ingredients are typically employed in the composition at levels that are effective at providing the benefits of the ingredient or ingredients, such as, for example, from about 0.001% to about 50%, from about 0.1% to about 40%, or from about 1% to about 35%, by weight of the composition. Solvents may include a liquid, gel or semi-solid material. The solvent may be water, a thixotropic material, paste, an alcohol, ethylene glycol monobutyl ether, mineral oil, esters, silicone fluids, isoparaffins, alkanes like hexane, toluene, xylenes, low molecular weight polyethylene glycols like PEG-200, glycerin, glycols, a non-flammable solvent, an adhesive material, or other organic species. Preferred non-aqueous solvents may comprise alcohols, acetates, and combinations thereof. The alcohol solvents are preferably selected from the group consisting of iso-propyl alcohol, n-propyl alcohol, ethanol, methanol, and combinations thereof. Likewise, suitable acetate solvents include, but are not limited to, isopropyl acetate, n-propyl acetate, and combinations thereof.

Other suitable solvents that may be effective include water, aqueous detergent solutions, acidic water solutions, alkaline water solutions, isopropanol, ethanol, methyl-ethyl ketone, acetone, toluene, hexane, ethyl 15 acetate, acetic acid (vinegar), cetyl alcohol (fatty alcohol), dimethicone silicone, iso-propyl lanolate, myristate, palmitate, lanolin, lanolin alcohols and oils, octyl dodecanol, oleic acid (olive oil), panthenol (vitamin B-complex derivative), stearic acid and stearyl alcohol, butylene glycol and propy lene glycol, cyclomethicone (volatile silicone), glycerin, aloe, petrolatum, and so forth. Viscous solvents, such as for example, common tape adhesives, have been found to be particularly effective at delaying or controlling the onset of the color change. Adhesives that may be useful include, for example, those based on alkyds, animal glues, casein glues, cellulose acetates, cellulose acetate butyrates, cellulose nitrates, ethyl celluloses, methyl celluloses, carboxy methyl celluloses, epoxy resins, furane resins, melamine resins, phenolic resins, unsaturated polyesters, polyethylacrylates, poly-methylmethacrylates, polystyrenes, polyvinylacetates, polyvinylalcohols, polyvinyl acetyls, polyvinyl chlorides, polyvinyl acetate chlorides, polyvinylidene copolymers, silicones, starched based vegetable glues, urethanes, acrylonitrile rubbers, polybutene rubbers, chlorinated rubbers, styrene rubbers, and so forth. Waxes such as, for example, polyolefin waxes, bees waxes, and so forth, and gels such as, for example, glycol dimethacrylate, chitosan, polyacrylates, hydroxypropylcellulose, gelatin, and so forth, may also be useful to effect the color change.

It may be desirable to include a stabilizer when the colorant is a pH indicator and when the absorbent article could be stored under conditions of high humidities and temperatures. The inclusion of a stabilizer is also especially important for new diaper designs where materials and/or chemicals are present that could potentially prematurely activate the color change of the colorant within the ink formulation.

In one embodiment of the present invention, the stabilizer is an acidic stabilizer. In another embodiment of the present invention, the stabilizer is a basic stabilizer. The inclusion of a stabilizer, while not wishing to be limited by theory, is believed to play a role in stabilizing the colorant against premature changes caused by exposure to humid environments and/or certain components of the diaper, by maintaining a stable pH, such as a low pH environment with an acidic stabilizer, around the colorant even when the system is exposed to high humidities and/or certain components of the diaper. This maintenance of a stable pH environment keeps the colorant, especially when the colorant is a pH indicator, in its initial dry color state. Desiccants can also stabilize the composition by trapping free water that could prematurely activate the wetness indicator composition. Examples of suitable desiccants include silica gel, bentonite clays, activated alumina, calcium sulfate, copper(II) sulfate, and magnesium sulfate.

One of the key properties of a properly functioning wetness indicator is for it to maintain its dry state color during a variety of storage and packaging conditions while still undergoing a noticeable color change in a reasonable amount of time after being contacted by urine. The colorant should also remain stable to various chemicals and materials that might be present in the diaper. Although acidic moieties present in the rosins as part of the matrix can aid in preserving the dry state color, additional stabilizer ingredients have been found to be necessary with some new diaper designs where high pH components within the diaper can cause the undesirable and premature color change activation of the colorant. To maintain the colorant in its acidic dry state color, acids of suitable strength should be added. Suitable strength is defined by the colorant and pH range where it changes color. The colorant's pKa value is especially important in assessing the characteristics of the chosen stabilizer.

For a pH indicator colorant like the sulfonephthalein class which includes bromocresol green which changes color between a pH of 3.8 and 5.4 (See "The Sigma-Aldrich Handbook of Stains, Dyes and Indicators," by Floyd J. Green, Aldrich Chemical Co., Milwaukee, Wis.), the stabilizer should contribute suitably strong acidic moieties to keep the bromocresol green in its yellow state within the matrix. Although many strong acids like sulfuric acid and hydrochloric acid have suitably low pH's to accomplish this, their solubilities are low in these anhydrous matrices. In addition, their high acidity can chemically decompose the structures of some of the components present in the wetness composition and diaper. As noted, carboxylic acid moieties present in the matrix ingredients like rosins or polymerized rosins can also aid in maintaining the colorant in its acidic color state but carboxylic acids are typically too weak to maintain the dry yellow state of bromocresol green if it is exposed to high humidities and/or high pH components within new diaper designs. To increase the strength of the carboxylic acids, one can add electron withdrawing groups between the carboxylic acid moiety and another portion of the molecule. Although a fatty acid like stearic acid can aid in preserving the dry state color, it can be made more effective by making it a stronger acid by inserting polyoxyethylene groups between the carboxylic acid group and the alkyl chain. These types of molecules are called ether carboxylates and these acidic molecules can be effective in maintaining the dry state acid form of the pH indicator colorant like bromocresol green. In addition, the alkyl group present in these ether carboxylates increases their solubility in the wetness indicator matrix. Finally, the ether carboxylate's surfactancy can aid in increasing the kinetics for activating the color change of the wetness indicator composition after it is contacted by urine.

Other suitable stabilizers are those of the monoalkyl phosphate free acid and dialkyl phosphate free acid types. The phosphate acid moiety is a stronger acid than the carboxylic acid group and thus can be more effective in maintaining the low pH environment required to keep the pH indicator colorant in its dry acidic state. These alkyl phosphate free acids have been found to be particularly effective in preserving the dry state color of the bromocresol green colorant from premature activation as caused by high humidities or destabilizing materials and/or chemicals present in new diaper designs. Particularly effective alkyl phosphate free acids are stearyl phosphate free acid, cetyl phosphate free acid, and cetearyl phosphate free acids. Thus, the phosphate is a suitably strong acid to maintain the pH indicator colorant in its acidic dry state form, and the lipophilic alkyl moiety aids in increasing its solubility within the wetness indicator composition. In addition, the surfactant nature of the alkyl phosphate free acids can aid in speeding up the kinetics of the color change after the wetness indicator composition is contacted by urine.

Other acidic stabilizers which are particularly effective in stabilizing the wetness indicator formula to high humidities and/or destabilizing components within the diaper include, but are not limited to: organic acids, such as, but not limited to, fatty acids such as stearic acid, palmitic acid, lower molecular weight acids such as citric acid, malic acid, maleic acid, lactic acid, glycolic acid, gluconic acid, fumaric acid, adipic acid, ascorbic acid, and salicylic acid; acid esters, such as, citrate esters, e.g., monostearyl citrate and monocetyl citrate, glycolate esters, lactate esters; phosphorus containing organic acids, such as, monostearyl phosphate and monocetyl phosphates; ether carboxylic acids; N-acyl sarcosinic acids; N-acyl glutamic acids; N-acyl ethylenediaminetriacetic acid; alkane sulfonic acids; alpha-olefin sulfonic acids; alpha-sulfonic acid fatty acid methyl esters; sulfate esters; inorganic acids, such as, phosphoric acid; and combinations thereof. Examples of suitable basic stabilizers include, but are not limited to: monoethanolamine; diethanolamine; triethanolamine; dipropylenetriamine; diiosopropyl amine; organic diamines, such as, but not limited to, 1,3-bis(methylamine)-cyclohexane, 1,3-pentanediamine; inorganic bases, such as, but not limited to, sodium hydroxide, magnesium hydroxide, and combinations thereof.

The stabilizer, when present is typically employed in compositions at levels which are effective at stabilizing the colorant, from about 0.001% to about 30%, from about 0.1% to about 15%, and also from about 1% to about 10%, by weight of the composition.

The present invention may include structural adjuncts, such as HLB (hydrophilic lipophilic balance) modifiers, viscosity modifiers, hardening agents, wetting agents, anti-oxidants, anti-leaching aids, and/or colorant solubilizers. Suitable ones may include polymeric thickeners such as block copolymers having polystyrene blocks on both ends of a rubber molecule, the aforementioned copolymers of ethylene and vinyl acetate (EVA), hydrogenated castor oil, polymers, metals salts of fatty acids, silicas and or derivatized silicas, organoclays such as modified and unmodified hectorites and bentonites, modified clays such as modified laponite clays, dibenzylidene sorbitol, alkyl galactomannan, aluminium magnesium hydroxide stearate/oil blends and lauroyl glutamic dibutylamide. Hardening agents may include the aforementioned waxes, C14-22 fatty alcohols, C14-22 fatty acids, C23-60 carboxylic acids, hydrogenated vegetable oils, polymers, sorbitan esters and other high molecular weight esters.

The wetting agent can be a surfactant or a mixture of surfactants. The wetting agent can also be an ester like Innospec's C12-15 alkyl benzoate. The wetting agent can comprise a combination of surfactants and esters. The surfactant wetting agent can be polyhydroxystearic acids like Innospec's Dispersun DSP-OL100™. The surfactants can be nonionic surfactants or ionic surfactants. The ionic surfactants can be either positively charged or negatively charged. The examples of non-ionic surfactants include alkyl poly(ethylene oxide) such as copolymers of poly(ethylene oxide) and poly(propylene oxide) (commercially called Poloxamers or Poloxamines), alkyl polyglucosides such as octyl glucoside and decyl maltoside, fatty alcohols such as cetyl alcohol, oleyl alcohol, cocamide MEA and cocamide DEA. The examples of ionic surfactants include anionic (e.g., based on sulfate, sulfonate or carboxylate anions) surfactants such as s(SDS), ammonium lauryl sulfate and other alkyl sulfate salts, Sodium laureth sulfate, also known as sodium lauryl ether sulfate (SLES), Alkyl benzene sulfonate, Soaps, or fatty acid salts; and Cationic (e.g., based on quaternary ammonium cations) surfactants such as Cetyl trimethylammonium bromide (CTAB) a.k.a. hexadecyl trimethyl ammonium bromide, and other alkyltrimethylammonium salts, Cetylpyridinium chloride (CPC), Polyethoxylated tallow amine (POEA), Benzalkonium chloride (BAC), Benzethonium chloride (BZT); or Zwitterionic (amphoteric) surfactants such as Dodecyl betaine, Dodecyl dimethylamine oxide, Cocamidopropyl betaine, Coco ampho glycinate. Alternatively, the wetting agents may also be hydrophilic molecules. The hydrophilic molecules may be small molecules such as sucrose, glucose and glycerol. The hydrophilic molecules may also be polymers such as polyethylene glycol and its copolymers.

Substrate

In one embodiment of the present invention, the liquid-activated formulation of the present invention may be on and/or in a substrate. When present on a substrate, the liquid-activated formulation will typically be placed on and/or in a substrate where the substrate will be contacted by a liquid, such as water, urine, menses, blood and the like. The substrate may include, but is not limited to, a structural component, such as woven fabrics, nonwoven fabrics, films, sponges, and combinations thereof. The substrate may comprise synthetic and/or natural materials. In one embodiment of the present invention the optional substrate may be an article in its own right, such as, a continuous nonwoven fabric. In another embodiment of the present invention the substrate to which the liquid-activated formulation may be applied or otherwise affixed comprises any one, or a combination of, structural components of an absorbent article, including, but not limited to, the backsheet, topsheet, fasteners, absorbent material, etc., or may be a separate element added or applied to the product. In one optional embodiment of the present invention the liquid-activated formulation is applied to the absorbent article as a whole. In some embodiments, the liquid-activated formulation is a single layer. Such a single layer may be applied to a substrate or structural component. In some embodiments, the single-layer formulation may be disposed between the backsheet and the absorbent core, in other embodiments, between the topsheet and the absorbent core.

The indicating material may be coated over a surface of said substrate as either a) a monochromic color scheme alone, bi-chromic, or multiple colors, b) in various shapes and sizes, c) graphics of patterns or alpha numeric symbols and words, or combinations thereof. The color transition may be from being either a) colored to uncolored, b) uncolored to colored, c) first color to second color or c) a combination of a) b) and c).

The manufacture of substrates, absorbent articles and structural components thereof, for use herein form no part of this invention. The following discussion is for convenience of formulation, but is not intended to limit the type of substrate used herein.

In one embodiment of the present invention the disposable absorbent article is a disposable diaper. Typically, modern disposable diapers comprise a liquid pervious topsheet; a liquid impervious backsheet; an absorbent core which may be positioned between at least a portion of the topsheet and the backsheet; side panels; elasticized leg cuffs; an elastic waist feature; and a fastening system. In one embodiment opposing sides of the disposable diaper may be seamed or welded to form a pant. This allows the article to be used as a pull-on type diaper, such as a training pant. Additional illustrative, but non-limiting, information on construction, assembly, and the various components (including backsheets, dusting layers, upper and lower covering sheets, and webs) of disposable diapers may be found in U.S. Pat. No. 3,860,003 to Buell; U.S. Pat. No. 5,151,092 to Buell; U.S. Pat. No. 5,221,274 to Buell; U.S. Pat. No. 5,554,145 to Roe et al. on Sep. 10, 1996; U.S. Pat. No. 5,569,234 to Buell et al.; U.S. Pat. No. 5,580,411 to Nease et al.; U.S. Pat. No. 6,004,306 to Robles et al.; U.S. Pat. No. 5,938,648 to LaVon et al.; U.S. Pat. No. 5,865,823 to Curro; U.S. Pat. No. 5,571,096 to Dobrin et al.; U.S. Pat. No. 5,518,801 to Chappell, et al.; U.S. Pat. No. 4,573,986 to Minetola et al.; U.S. Pat. No. 3,929,135, to Thompson; U.S. Pat. No. 4,463,045 to Ahr, et al.; U.S. Pat. No. 4,609,518 to Curro et al.; U.S. Pat. No. 4,629,643 to Curro et al.; U.S. Pat. No. 5,037,416 to Allen et al.; U.S. Pat. No. 5,269,775 to Freeland et al.; U.S. Pat. No. 4,610,678 to Weisman et al.; U.S. Pat. No. 4,673,402 to Weisman et al.; U.S. Pat. No. 4,888,231 to Angstadt; U.S. Pat. No. 5,342,338 to Roe; U.S. Pat. No. 5,260,345 to DesMarais et al.; U.S. Pat. No. 5,026,364 to Robertson; U.S. Pat. No. 3,848,594 to Buell; U.S. Pat. No. 4,846,815 to Scripps; U.S. Pat. No. 4,946,527 to Battrell; U.S. Pat. No. 4,963,140 to Robertson et al.; U.S. Pat. No. 4,699,622 to Toussant et al.; U.S. Pat. No. 5,591,152 to Buell et al.; U.S. Pat. No. 4,938,753 to Van Gompel, et al.; U.S. Pat. No. 5,669,897 to LaVon, et al.; U.S. Pat. No. 4,808,178 to Aziz et al.; U.S. Pat. No. 4,909,803 to Aziz et al.: U.S. Pat. No. 4,695,278 to Lawson and U.S. Pat. No. 4,795,454 issued to Dragoo; and U.S. Ser. No. 10/770,043 to LaVon; U.S. Pat. No. 7,318,820 to LaVon et al.; U.S. Pat. No. 6,962,578 to LaVon; U.S. Pat. No. 7,377,914 to LaVon; Ser. No. 11/715,976 to LaVon; Ser. No. 10/880,128 to LaVon; Ser. No. 11/131,799 to LaVon et al., Ser. No. 11/133,818 to LaVon et al.; Ser. No. 11/135,689 to LaVon; Ser. No. 11/140,888 to LaVon et al.; Ser. No. 11/158,563 to LaVon et al.; Ser. No. 11/159,916 to LaVon et al., Ser. No. 11/197,197 to LaVon et al.; Ser. No. 11/210,345 to LaVon et al.; Ser. No. 11/224,462 to LaVon et al.; Ser. No. 11/231,511 to LaVon et al.; Ser. No. 11/231,512 to LaVon et al.; Ser. No. 11/231,500 to LaVon et al.; U.S. Pat. No. 7,320,684 to LaVon et al.; Ser. No. 11/286,934 to LaVon et al.; Ser. No. 11/286,614 to LaVon; Ser. No. 11/286,612 to LaVon; Ser. No. 11/700,585 to LaVon et al.; Ser. No. 11/709,500 to LaVon et al.; Ser. No. 11/713,906 to LaVon et al.; Ser. No. 11/728,127 to LaVon et al.; 61/073,154 to LaVon; and 61/073,169 to LaVon; US Pub. Nos. 2004/0162536 to Becker filed on Feb. 11, 2004; 2007/0167928 to Becker filed on Mar. 13, 2007; 2007/0179464 to Becker filed on Mar. 13, 2007; 2007/0156108 to Becker filed on Mar. 13, 2007; and 2004/0167486 to Busam filed on Feb. 11, 2004; U.S. Ser. Nos. 60/936,102 to Hundorf filed on Jun. 18, 2007; 60/936,109 to Hundorf filed on Jun. 18, 2007; 60/936,149 to Hundorf filed on Jun. 18, 2007; 60/936,085 to Ashton filed on Jun. 18, 2007; 60/936,084 to Ashton filed on Jun. 18, 2007; 60/936,150 to Ashton filed on Jun. 18, 2007; 60/936,146 to Asthon filed on Jun. 18, 2007; 60/936,037 to Ashton filed on Jun. 18, 2007; and 61/091,799 to Hundorf filed on Aug. 26, 2008.

In one alternative embodiment of the present invention a portion of the absorbent article, such as part or all of the topsheet, part or all of the barrier leg cuffs and the like, may be optionally coated with a lotion, as is known in the art. Examples of suitable lotions include, but are not limited to, those described in U.S. Pat. No. 5,607,760 to Roe on; U.S. Pat. No. 5,609,587 to Roe; U.S. Pat. No. 5,635,191 to Roe et al.; U.S. Pat. No. 5,643,588 to Roe et al.; and U.S. Pat. No. 5,968,025 to Roe et al.

The liquid-activated colorant may be included in the liquid activated formulation at a level which is within the range of about 0.01 weight percent to about 20 weight percent, or may be incorporated into the liquid activated formulation at a level which is within the range of about 0.02 weight percent to about 15 weight percent, based upon the total weight of the liquid activated formulation. The liquid activated colorant may be included in the liquid activated formulation at a level which is within the range of about 0.02 weight percent to about 10 weight percent, or may be incorporated into the liquid activated formulation at a level which is within the range of about 0.02 weight percent to about 2 weight percent.

The hydrochromic ionic compound may be included in the liquid activated formulation at a level which is within the range of about 0.01 weight percent to about 35 weight percent, or may be incorporated into the liquid activated formulation at a level which is within the range of about 0.1 weight percent to about 30 weight percent, based upon the total weight of the liquid activated formulation. The hydrochromic ionic compound may be included in the liquid activated formulation at a level which is within the range of about 0.1 weight percent to about 25 weight percent, or may be incorporated into the liquid activated formulation at a level which is within the range of about 0.1 weight percent to about 20 weight percent.

The opacifier may be included in the liquid activated formulation at a level which is within the range of about 0.5 weight percent to about 75 weight percent or may be incorporated into the liquid activated formulation at a level which is within the range of about 10 weight percent to about 50 weight percent, based upon the total weight of the liquid activated formulation. The opacifier may be included in the liquid activated formulation at a level which is within the range of about 20 weight percent to about 45 weight percent, or may be incorporated into the liquid activated formulation at a level which is within the range of about 30 weight percent to about 40 weight percent.

In some embodiments, the liquid-activated colorant may be about 0.1 weight percent of the liquid-activated formulation, or may be from about 0.01 to about 5 weight percent of the liquid-activated formulation. In some embodiments, the opacifier may be from about 0.5 to about 60 wt % of the liquid-activated formulation. For opacifiers such as or similar to titanium dioxide, the weight percent may be from about 0.5% to about 2%. For opacifiers such as or similar to aluminum silicate, the weight percent may be from about 30% to about 70%. In some embodiments, the hydrochromic ionic compound may be present in the liquid-activated formulation about 0.1 wt % or from about 0.05 wt % to 0.15 wt % for a strong base like sodium hydroxide or a strong acid like hydrochloric acid. For weaker acids and bases, the hydrochromic ionic compound may have a weight percent of about 10% or be in a range of from about 2% to about 18%. In some embodiments, the binding matrix may be from about 25 wt % to about 75 wt % of the liquid-activated formulation.

EXAMPLE

The present invention is illustrated by the following examples, which are merely for the purpose of illustration and are not to be regarded as limiting the scope of the invention or the manner in which it can be practiced. Unless specifically indicated otherwise, parts and percentages are given by weight. Examples may include any of the compositions and components disclosed in U.S. Patent Application Ser. No. 61/705,861, titled "Liquid Activated Color Change Ink and Methods of Use".

Example 1

| EXAMPLE 1 | | | |
|---|---|---|---|
| Sodium Aluminum Silicate | 50.40% | Sipernat 820A | Opacifier/Evonik |
| Aerosol OT-100 | 22.00% | Sodium dioctylsulfosuccinate | Surfactant/Cytec Industries |
| Polyhydroxystearic acid | 2.00% | Dispersun DSP-OL100 | Particle Wetting Agent/Innospec Inc. |
| Ethylene vinyl acetate | 12.00% | Ellvax ® 40W | Binder Base Material/DuPont ™ |
| Arquad ® HTL-8 MS | 2.00% | Stearyl Ethylhexyldimonium Methosulfate | Quaternary Anti-Leaching Aid/AkzoNobel |
| Sodium hydrogen carbonate | 11.00% | | hydrochromic ionic compound/Sigma-Aldrich |
| Bromocresol Green, free acid | 0.20% | | Colorant/Curtiss Labs |
| Irganox 1010 | 0.40% | Tetrakis[methylene(3,5-di-(tert)-butyl-4-hydroxyhydrocinnamate)]methane | Anti-Oxidant/Ciba Inc. |
| | 100.00% | | |
| EXAMPLE 2 | | | |
| Sodium Aluminum Silicate | 51% | Sipernat 820A | Opacifier/Evonik |
| Tergitol ® 15-S-9 Dow Chemical | 7% | | Surfactant/Dow |
| EB (Ethyleneglycol monbutyl Ether) | 7% | | |
| Water based binder (Joncryl 624) | 21% | | Binder Base Material/BASF |
| m-cresol purple | 0.5% | | Colorant/Sigma-Aldrich |
| Sodium hydroxide (50% solution) | 1.5% | | Hydrochromic ionic compound/Sigma-Aldricj |
| Water | 11.7% | | Solvent |
| Irganox 1010 | 0.3% | Tetrakis[methylene(3,5-di-(tert)-butyl-4-hydroxyhydrocinnamate)]methane | Anti-Oxidant/Ciba |

Examples may be prepared in the following manner:

Those ingredients that are solids at room temperature are first melted at a temperature of around 90 C. These ingredients include the binding agents, hot melt adhesives, waxes, surfactants, and optional ingredients like the anti-oxidants. Typically, a temperature of around 80 C to 100 C would be required to melt these ingredients. After melting to the liquid state on a hot plate, the materials are well mixed using a propeller mixer like an IKA RW-20 (or similar mixer) until the mixture is homogeneous. While keeping this mixture heated and mixed, the Sodium Aluminum Silicate powder is homogeneously mixed into the composition. Next, the hydrochromic ionic compound, sodium hydrogen carbonate, is mixed into the composition while maintaining heating. Finally, the colorant like bromocresol green (free acid) is well mixed into the composition until the mixture is homogeneous. Heat can be maintained on the composition to make films using a draw-down wire or the composition can be cooled down to room temperature for future use.

Example 3

| Ingredient | Wt (g) | Wt (%) | |
|---|---|---|---|
| Joncryl 624 | 3.95 | 17.66% | Acrylic Polymer |
| Water | 9.43 | 42.17% | Dihydrogen Oxide |
| Sipernat 820a | 4.94 | 22.09% | Aluminum Silicate |
| m-cresol purple | 0.011 | 0.05% | |
| HTL8-MS | 0.87 | 3.89% | Quaternary Amine |
| NaOH/50% | 0.38 | 1.70% | |
| Tween 80 | 2.78 | 12.43% | Surfactant/emulsifier = Polyoxyethylene (20) sorbitan monooleate |
| TOTAL | 22.361 | 100.00% | |

Figure 2:
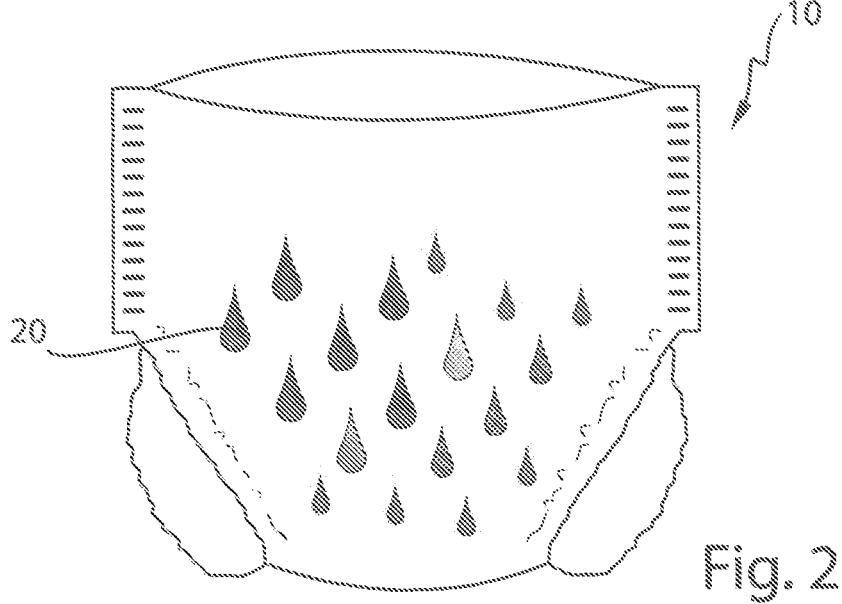
FIG. 2 is a front view of an absorbent article according to an aspect of the invention.
Figure 3:
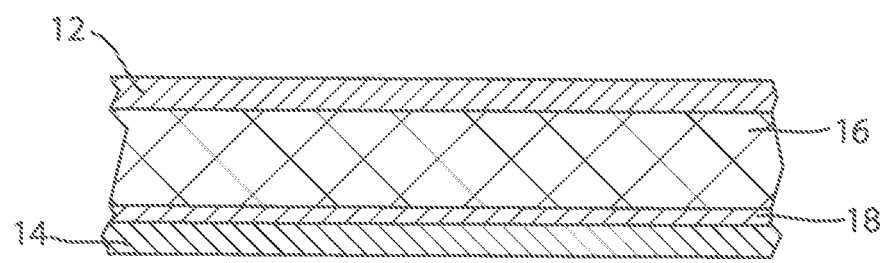
FIG. 3 is a cross section of an absorbent article of FIG. 1 according to an aspect of the invention.

According to an aspect of the invention, FIGS. 1-3 show an absorbent article 10 in an unfastened and uncontracted state that has a liquid permeable topsheet 12, a liquid impermeable backsheet 14, a liquid absorbent core 16 disposed between the topsheet 12 and the backsheet 14, further comprising a liquid indicator 20. The liquid indicator 20 comprises a coating 18 of liquid indicating ink disposed on the backsheet 14, between the backsheet 14 and the absorbent core 16, such that it is visually revealed when the coating 18 is wetted with body fluids. The liquid indicator is the liquid-activated formulation as described above. This liquid indicator may change color entirely when in contact with liquid, or may change noticeable shades of color, or may change from an almost white (so as it appears that there is no colorant there) to a color, or may change from a color to a white/colorless state. FIG. 2 shows an example of how the absorbent article may appear when wet, wherein the liquid indicator 20 appears in a raindrop pattern that is visible when wet. The liquid-activated formulation may be a single layer.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

We claim:

1. A single-layer liquid activated formulation comprising: (A) a liquid-activated colorant; (B) a hydrochromic ionic compound; (C) from about 20% to about 45% by weight an opacifier; and (D) a binding matrix; and (E) a surfactant.

2. The liquid-activated formulation of claim 1, wherein the formulation comprises from about 1% to about 30% by weight of the surfactant.

3. The liquid-activated formulation of claim 1, wherein the surfactant is an ethoxylated alcohol.

4. The liquid-activated formulation of claim 1, wherein the binding matrix is a hot melt binding matrix.

5. The liquid-activated formulation of claim 1, wherein the binding matrix is a solvent-based binding matrix.

6. The liquid-activated formulation of claim 1, further comprising a permanent colorant.

7. The liquid-activated formulation of claim 1, further comprising one or more selected from the group consisting of a stabilizer and/or a structural adjunct.

8. The liquid-activated formulation of claim 7, wherein said stabilizer is selected from the group consisting of monostearyl phosphate, citrate esters, alcohol ethoxycarboxylates, glycolate esters, lactate esters, fatty acids, ether carboxylic acids, fatty acid methyl esters, sulfate esters, fruit acids, citric acid, malic acid, inorganic acids, sulfuric acid, monoethanolamine, diethanolamine, triethanolamine, dipropyllenetriamine, diiosopropyl amine, 1,3-bis(methylamine)-cyclohexane, 1,3Pentanediamine, sodium hydroxide, magnesium hydroxide, and combinations thereof.

9. The liquid-activated formulation of claim 7, wherein said structural adjunct is selected from the group consisting of HLB modifiers, viscosity modifiers, hardening agents, and combinations thereof.

10. An absorbent article comprising the liquid-activated formulation of claim 1, wherein said liquid-activated formulation is affixed to a structural component of the absorbent article.

11. An absorbent article comprising the liquid-activated formulation of claim 1, wherein the article comprises a backsheet, a topsheet, an absorbent core disposed between the backsheet and the topsheet, wherein the liquid-activated formulation is a single layer and disposed between the backsheet and the absorbent core.

12. An absorbent article comprising the liquid-activated formulation of claim 1, wherein the article comprises a backsheet, a topsheet, an absorbent core disposed between the backsheet and the topsheet, wherein the liquid-activated formulation is a single layer and disposed between the topsheet and the absorbent core.

13. The liquid activated formulation as specified in claim 1 wherein the liquid activated colorant is selected from the group consisting of Malachite green, brilliant green, crystal violet, erythrosine B, methyl green, methyl violet 2D, picric acid, naphthol yellow S, quinaldine red, eosine Y, metanil yellow, m-cresol purple, thymol blue, xylenol blue, basis fuchsin, eosin B, 4-p-aminophenol(azo)benzenesulphonic acid-sodium salt, cresol red, martius yellow, phloxine B, methyl yellow, bromophenol blue, congo red, methyl orange, bromochlorophenol blue (water soluble or free acid form), ethyl orange, flourocene WS, bromocresol green, chrysoidine, methyl red sodium salt, alizarine red S-H2O, cochineal, chlorophenol red, bromocresol purple, 4-naphtha, alizarin, nitrazine yellow, bromothymol blue, brilliant yellow, neutral red, rosalic acid, phenol red, 3-nitro phenol, orange II, phenolphthalein, o-cresolphthalein, nile blue A, thymolphthalein, aniline blue WS, alizarine yellow GG, mordant orange, tropaolin O, orange G, acid fuchsin, thiazol yellow G, indigo carmine, FD&C Blue No. 1, FD&C Blue No. 2, FD&C Green No. 3, FD&C Red No. 40, FD&C Red No. 4, FD&C Yellow No. 5, FD&C Yellow No. 6, C.I. Food Blue 5, and C.I. Food Red 7, D&C Yellow No. 10, D&C Yellow No. 7, D&C Yellow No. 2, D&C Yellow No. 8, D&C Orange No. 4, D&C Red No. 22, D&C Red No. 28, D&C Red No. 33, D&C Green No. 8, D&C Green No. 5, D&C Brown No. 1, bromopyrogallol red, bromoxylenol blue, methylene blue, monoazo dyes, and any combination thereof.

14. The liquid activated formulation as specified in claim 1 wherein the hydrochromic ionic compound is selected from the group consisting of lithium hydrogen sulfate, lithium hydrogen carbonate, potassium hydrogen sulfate, potassium hydrogen carbonate, rubidium hydrogen sulfate, rubidium hydrogen carbonate, cesium hydrogen sulfate, cesium hydrogen carbonate, sodium hydrogen sulfate, sodium hydrogen carbonate, sodium carbonate, cesium hydroxide, lithium hydroxide, potassium hydroxide, calcium hydroxide, magnesium hydroxide, sodium thiosulfate penta hydrate, sodium hydroxide, rubidium hydroxide, cobalt chloride, cobalt nitrate, copper sulphate copper nitrate, iron (II) sulfate, iron (III) sulfate, iron (II) chloride, iron (III) chloride, sodium aluminum silicate, citric acid, monosodium dihydrogen citrate, disodium hydrogen citrate, trisodium citrate, gluconic acid, sodium gluconate, glycolic acid, sodium glycolate, malic acid, sodium malate, maleic acid, sodium maleate, acetic acid, phosphoric acid, trisodium phosphate, sodium dihydrogen phosphate, disodium hydrogen phosphate, monostearyl phosphate, monocetyl phosphate, monostearyl citrate, hydrochloric acid, nitric acid, sulfuric acid and combinations thereof.

15. The liquid activated formulation as specified in claim 1 wherein the opacifier is selected from the group consisting of titanium dioxide, calcium carbonate, calcium hydroxide, sodium silicate, potassium silicate, silica, starch, ethocell, methocell, barium carbonate, barium silicate, calcium silicate, aluminum silicate, aluminum hydroxide, aluminum oxide, sodium aluminum silicate, zirconium silicate, magnesium aluminum silicate, and styrene/acrylate copolymers.

16. The liquid activated formulation as specified in claim 1 wherein the a liquid activated colorant is present in the liquid activated formulation in an amount which is within the range of about 0.01 weight percent to about 20 weight percent, wherein the hydrochromic ionic compound is present in the liquid activated formulation in an amount which is within the range of about 0.05 weight percent to about 35 weight percent, and wherein the binding matrix is present in the liquid activated formulation in an amount which is within the range of about 5 weight percent to about 75 weight percent, based upon the total weight of the liquid activated formulation and wherein the surfactant is present in the liquid activated formulation in an amount which is within the range of about 1 weight percent to about 30 weight percent.

17. The liquid-activated formulation of claim 1, wherein the liquid-activated formulation has a color transition selected from the group consisting of a) colored to uncolored, b) uncolored to colored, c) colored to a different color, or d) a combination of a) and b) and c).

* * * * *